(12) United States Patent
Ueno et al.

(10) Patent No.: US 8,512,230 B2
(45) Date of Patent: Aug. 20, 2013

(54) ATTACHMENT AND DETACHMENT MECHANISM

(75) Inventors: Haruhiko Ueno, Akiruno (JP); Yutaka Masaki, Mitaka (JP)

(73) Assignee: Olympus Medical Systems Corp. (JP)

( * ) Notice: Subject to any disclaimer, the term of this patent is extended or adjusted under 35 U.S.C. 154(b) by 1203 days.

(21) Appl. No.: 12/134,653

(22) Filed: Jun. 6, 2008

(65) Prior Publication Data

US 2008/0310912 A1 Dec. 18, 2008

(30) Foreign Application Priority Data

Jun. 12, 2007 (JP) .................. 2007-155551

(51) Int. Cl.
*A61B 1/00* (2006.01)
(52) U.S. Cl.
USPC ............ 600/136; 600/145; 600/146; 600/147
(58) Field of Classification Search
USPC ............... 600/136, 145–147; 403/322.1, 361
See application file for complete search history.

(56) References Cited

U.S. PATENT DOCUMENTS

| | | | | | |
|---|---|---|---|---|---|
| 4,273,486 | A | * | 6/1981 | Tatina .......................... | 410/103 |
| 5,511,893 | A | * | 4/1996 | Kilgus et al. .................. | 403/294 |
| 6,811,348 | B1 | * | 11/2004 | Meyer et al. ................... | 403/325 |
| 7,828,723 | B2 | * | 11/2010 | Ueno et al. .................... | 600/136 |
| 2001/0037051 | A1 | * | 11/2001 | Fujii et al. ..................... | 600/146 |
| 2002/0103418 | A1 | * | 8/2002 | Maeda et al. .................. | 600/152 |

FOREIGN PATENT DOCUMENTS

| | | |
|---|---|---|
| JP | 5-300870 | 11/1993 |
| JP | 6-193640 | 7/1994 |
| JP | 6-217928 | 8/1994 |
| JP | 7-194516 | 8/1995 |
| JP | 2002-224016 | 8/2003 |
| WO | WO 2006/059721 | 6/2006 |
| WO | WO 2006/059721 A1 | 6/2006 |

OTHER PUBLICATIONS

European Search report dated Sep. 2, 2008.
Office Action issued by the Japanese Patent Office on Feb. 7, 2012 in connection with corresponding Japanese Patent Application No. 2007-155551.
Translation of Office Action issued by the Japanese Patent Office on Feb. 7, 2012 in connection with corresponding Japanese Patent Application No. 2007-155551.

* cited by examiner

*Primary Examiner* — Katherine Dowe
*Assistant Examiner* — Kevin G Barry, III
(74) *Attorney, Agent, or Firm* — Ostrolenk Faber LLP

(57) ABSTRACT

An attachment and detachment mechanism includes convex and concave engaging portions provided in first and second couplings respectively and extending in a radial direction of first and second shaft portions, the convex engaging portion is to be slidably inserted into and removed from the concave engaging portion along a longitudinal direction of the concave engaging portion, the convex and concave engaging portions includes basic positions where the longitudinal directions of the convex and concave engaging portions correspond to the attachment and detachment direction of the first and second main body portions and the convex and concave engaging portions are insertable into and removable from each other, and the attachment and detachment mechanism further includes a guide mechanism to guide one engaging portion such that the one engaging portion is disposed at the basic position in conjunction with the attachment or detachment of the first and second main body portions.

15 Claims, 11 Drawing Sheets

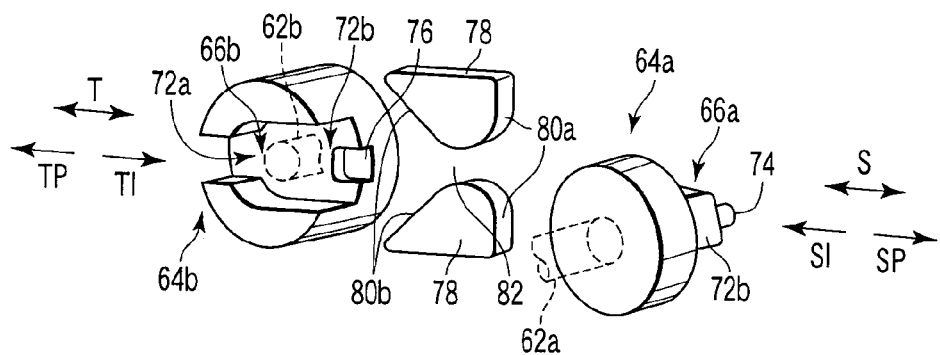
F I G. 3
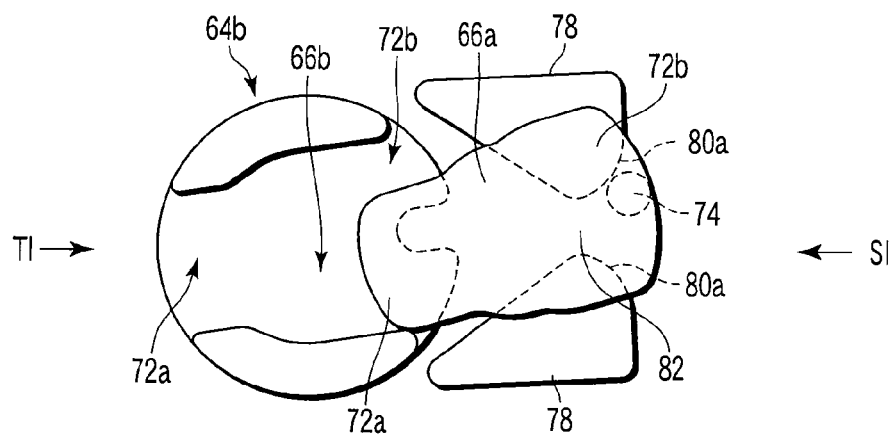
F I G. 4
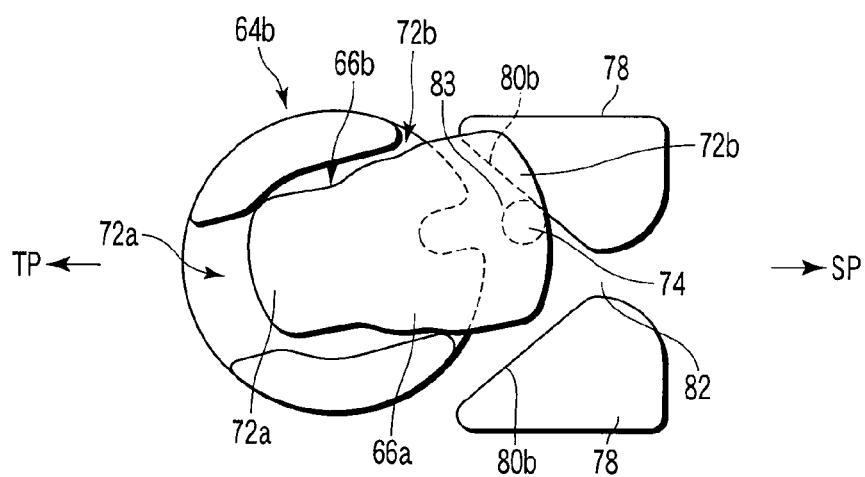
F I G. 5

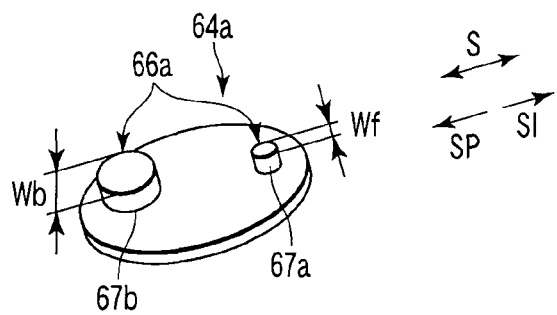
F I G. 11
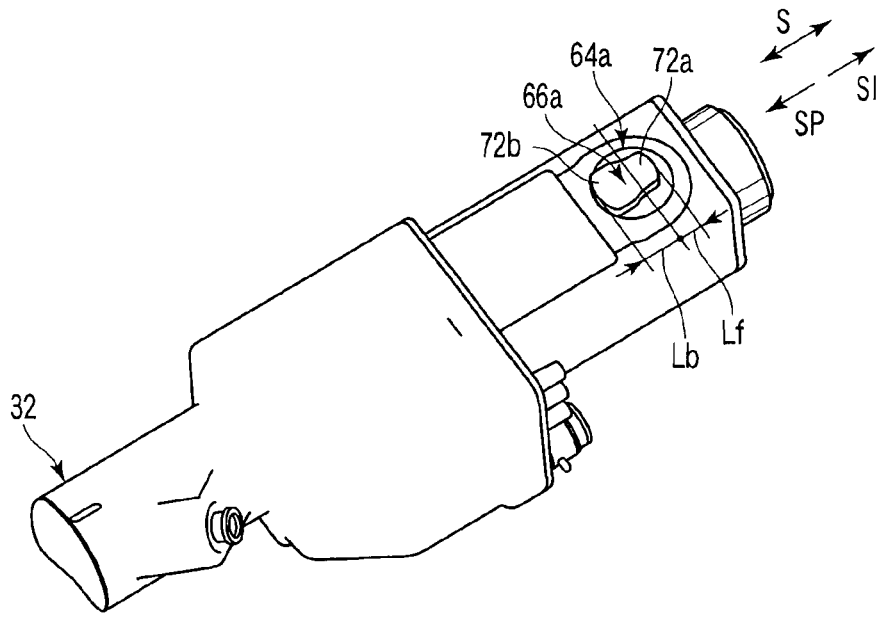
F I G. 12
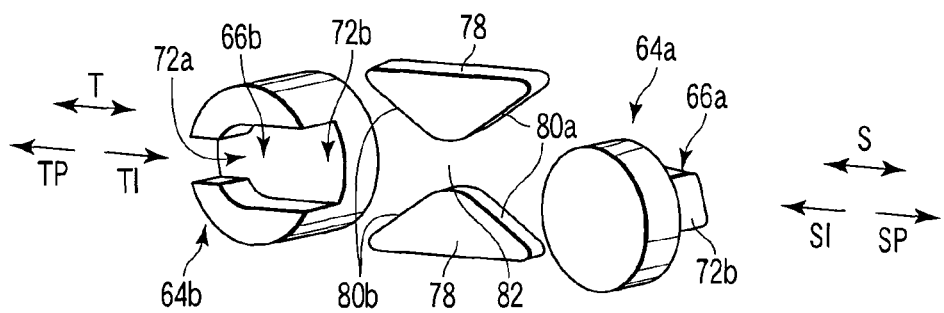
F I G. 13

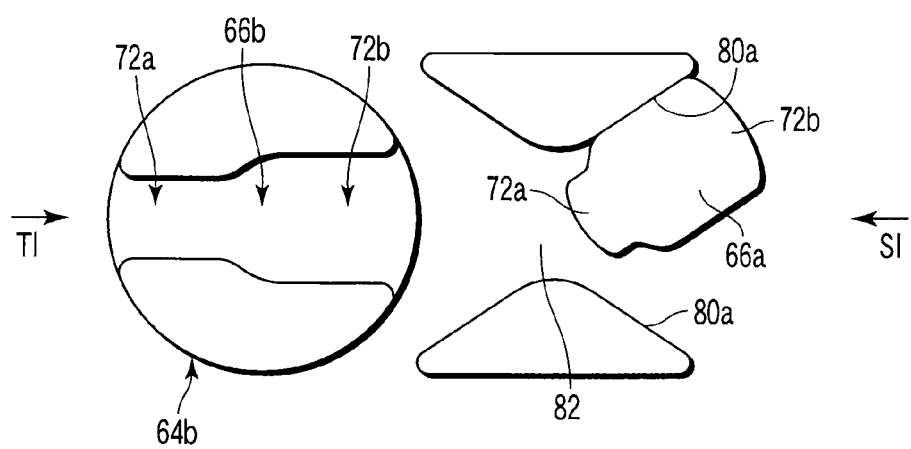
F I G. 14
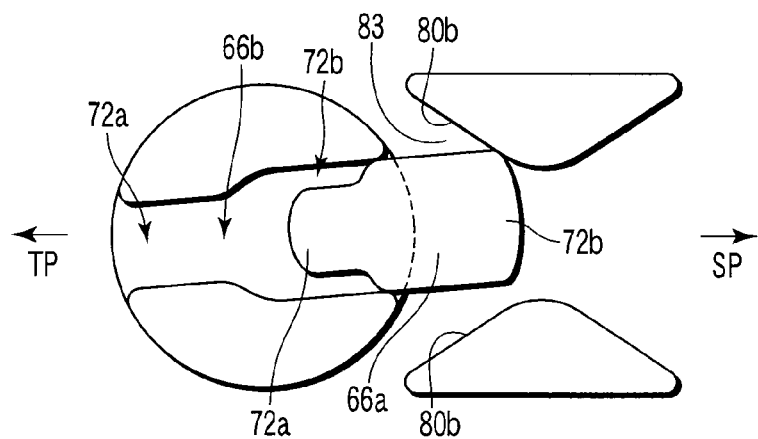
F I G. 15

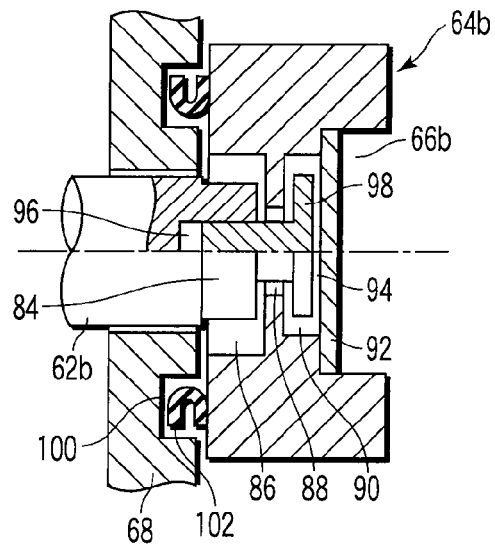
F I G. 16
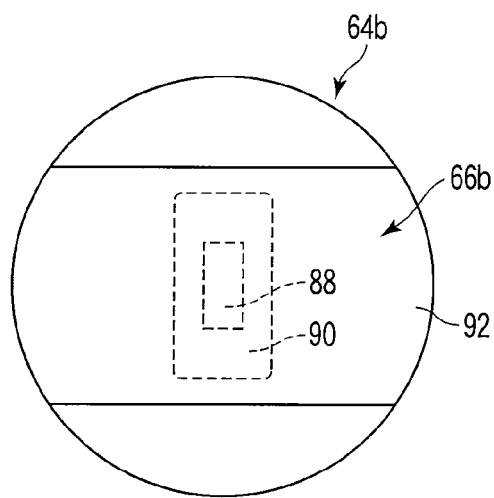
F I G. 17
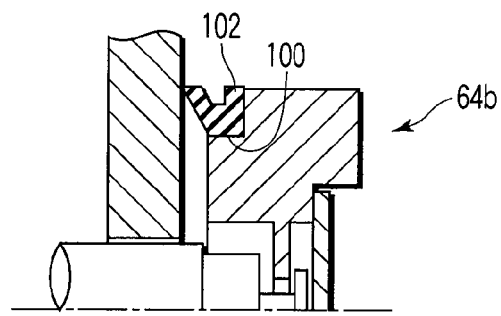
F I G. 18

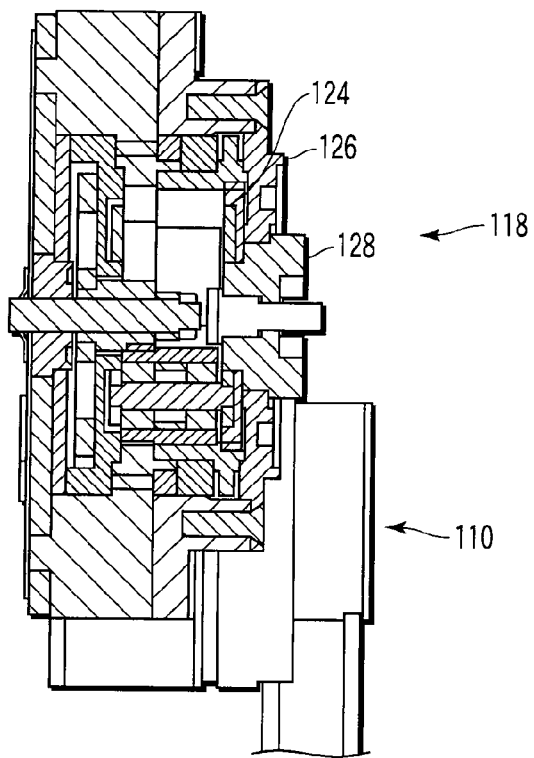
F I G. 21
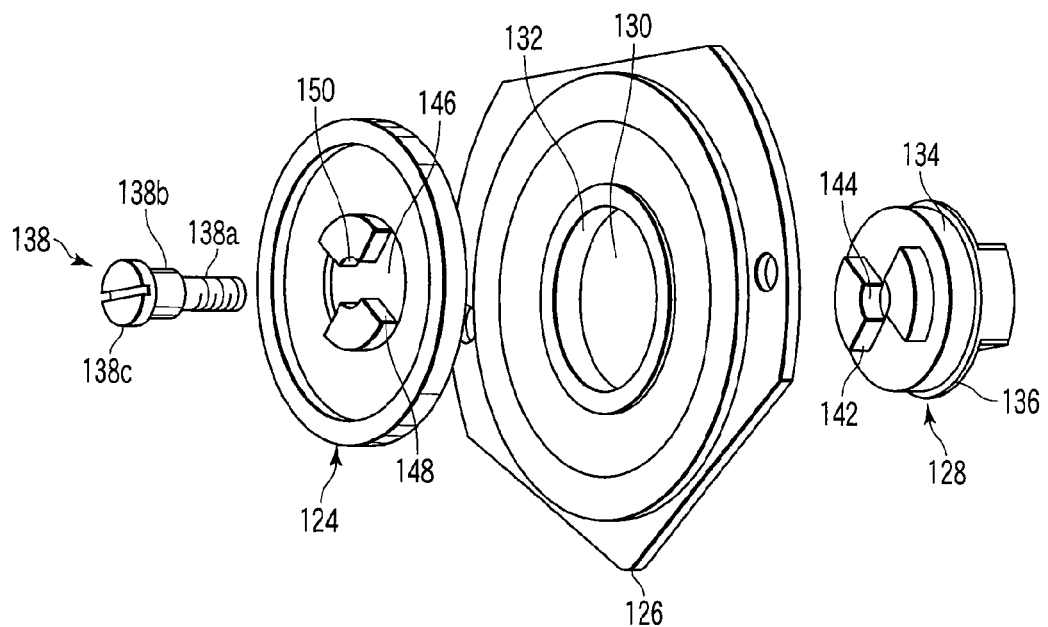
F I G. 22

ATTACHMENT AND DETACHMENT MECHANISM

CROSS-REFERENCE TO RELATED APPLICATIONS

This application is based upon and claims the benefit of priority from prior Japanese Patent Application No. 2007-155551, filed Jun. 12, 2007, the entire contents of which are incorporated herein by reference.

BACKGROUND OF THE INVENTION

1. Field of the Invention

The present invention relates to an attachment and detachment mechanism including a driving side coupling and a driven side coupling to be coupled to and separated from each other in an attachment and detachment of a driving side main body and a driven side main body.

2. Description of the Related Art

There has been conventionally used an attachment and detachment mechanism including a driving side coupling and a driven side coupling to be coupled to and separated from each other in an attachment and detachment of a driving side main body and a driven side main body.

Endoscopes including such attachment and detachment mechanisms are disclosed, for example, in Jpn. Pat. Appln. KOKAI Publication No. 2002-224016 and International Publication No. 2006/59721 pamphlet. Each of these endoscopes includes a motor unit and an insertion portion to be attached to or detached from each other. In the motor unit, a circular-plate-shaped driving side coupling is coaxially coupled to the terminal end portion of a driving side shaft portion. On the other hand, in the elongate insertion portion to be inserted into a body cavity, a circular-plate-shaped driven side coupling is coaxially coupled to the terminal end portion of a driven side shaft portion at the proximal end portion of the insertion portion, while a bending portion to be bent by the rotation of the driven side shaft portion is provided at the terminal end portion of the insertion portion.

In the attachment and detachment mechanism of Jpn. Pat. Appln. KOKAI Publication No. 2002-224016, an engaging concave portion extends in the radial direction of the driving side shaft portion in a terminal end face of the driving side coupling, an engaging convex portion extends in the radial direction of the driven side shaft portion in a terminal end face of the driven side coupling, and the engaging convex portion is to be slidably inserted into and removed from the engaging concave portion along the longitudinal direction of the engaging concave portion. The engaging convex portion is inserted into and removed from the engaging concave portion and so the driving side coupling and the driven side coupling are coupled to and separated from each other.

In the attachment and detachment mechanism in the International Publication No. 2006/59721 pamphlet, engaging concave portions and engaging convex portions are provided sequentially in a circumferential direction in terminal end faces of a driving side coupling and a driven side coupling. Further, a pin protrudes from the terminal end face of the certain engaging convex portion of the driven side coupling of the insertion portion, and a pin guide is provided in the motor unit. In the attachment of the motor unit and the insertion portion, when the driving side coupling and the driven side coupling are moved to face each other, the pin of the driven side coupling is guided by the pin guide of the motor unit and so the engaging concave portions and engaging convex portions of the driven side coupling are disposed opposite to the engaging convex portions and engaging concave portions of the driving side coupling, and then, when an engaging and separation button is operated, the driving side coupling is axially moved to the driven side coupling and so the driving side coupling and the driven side coupling are coupled to each other. On the other hand, in the removal of the motor unit and the insertion portion, the engaging and separation button is operated and so the driving side coupling is axially moved from the driven side coupling, and the driving side coupling and the driven side coupling are thus separated from each other.

BRIEF SUMMARY OF THE INVENTION

In an aspect of the present invention, an attachment and detachment mechanism includes: a first main body portion; a first shaft portion including a terminal end portion and a proximal end portion, the proximal end portion of the first shaft portion being supported by the first main body portion rotatably about a central axis of the first shaft portion; a first coupling provided at the terminal end portion of the first shaft portion; a convex engaging portion provided in the first coupling and extending in a radial direction of the first shaft portion; a second main body portion to be attached to and detached from the first main body portion; a second shaft portion including a terminal end portion and a proximal end portion, the proximal end portion of the second shaft portion being supported by the second main body portion rotatably about a central axis of the second shaft portion; a second coupling provided at the terminal end portion of the second shaft portion; and a concave engaging portion provided in the second coupling and extending in a radial direction of the second shaft portion, wherein the convex engaging portion is to be slidably inserted into and removed from the concave engaging portion along a longitudinal direction of the concave engaging portion, the convex and concave engaging portions includes basic positions where the longitudinal directions of the convex and concave engaging portions correspond to an attachment and detachment direction of the first and second main body portions and the convex and concave engaging portions are insertable into and removable from each other, and the attachment and detachment mechanism further comprises a guide mechanism to guide one engaging portion such that the one engaging portion is disposed at the basic position in conjunction with the attachment or detachment of the first and second main body portions.

In an aspect of the present invention, an endoscope includes: a drive unit forming one of a first main body portion and a second main body portion to be attached to and detached from each other; an insertion portion forming the other of the first main body portion and the second main body portion; a first shaft portion including a terminal end portion and a proximal end portion, the proximal end portion of the first shaft portion being supported by the first main body portion rotatably about a central axis of the first shaft portion; a first coupling provided at the terminal end portion of the first shaft portion; a convex engaging portion provided in the first coupling and extending in a radial direction of the first shaft portion; a second shaft portion including a terminal end portion and a proximal end portion, the proximal end portion of the second shaft portion being supported by the second main body portion rotatably about a central axis of the second shaft portion; a second coupling provided at the terminal end portion of the second shaft portion; and a concave engaging portion provided in the second coupling and extending in a radial direction of the second shaft portion, wherein the convex engaging portion is to be slidably inserted into and removed from the concave engaging portion along a longitudinal direction of the concave engaging portion, the convex and concave engaging portions includes basic positions where the longitudinal directions of the convex and concave engaging portions correspond to an attachment and detachment direction of the first and second main body portions and the convex and concave engaging portions are insertable into and removable from each other, the attachment and detachment mechanism further comprises a guide mechanism to guide one engaging portion such that the one engaging portion is disposed at the basic position in conjunction with the attachment or detachment of the first and second main body portions, the drive unit includes a drive portion to rotate one shaft portion, and the insertion portion includes a bending portion to be bent by the rotation of the other shaft portion.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a schematic diagram showing an insertion and removal mechanism in the first embodiment of the present invention;

FIG. 4 is a schematic diagram showing the insertion of the insertion and removal mechanism in the first embodiment of the present invention;

FIG. 5 is a schematic diagram showing the removal of the insertion and removal mechanism in the first embodiment of the present invention;

FIG. 11 is a perspective view showing a driven side coupling in a first modification of the second embodiment of the present invention;

FIG. 12 is a perspective view showing an insertion and removal portion in a second modification of the second embodiment of the present invention;

FIG. 13 is a schematic diagram showing an insertion and removal mechanism in the second modification of the second embodiment of the present invention;

FIG. 14 is a schematic diagram showing the insertion of an insertion and removal mechanism in the second modification of the second embodiment of the present invention;

FIG. 15 is a schematic diagram showing the removal of the insertion and removal mechanism in the second modification of the second embodiment of the present invention;

FIG. 16 is a longitudinal sectional view showing a driving side of a coupling mechanism in a third embodiment of the present invention;

FIG. 17 is a top view showing a driving side coupling of the coupling mechanism in the third embodiment of the present invention;

FIG. 18 is a longitudinal sectional view showing a driving side of a coupling mechanism in a fourth embodiment of the present invention;

FIG. 21 is a sectional view showing a driving mechanism in the referential embodiment of the present invention cut along the XXI-XXI line in FIG. 19;

FIG. 22 is an exploded perspective view showing a support structure of a gear shaft in the referential embodiment of the present invention;

DETAILED DESCRIPTION OF THE INVENTION

Hereinafter, embodiments of the present invention will be described with reference to the drawings.

FIGS. 1 to 5 show a first embodiment of the present invention.

Figure 1:
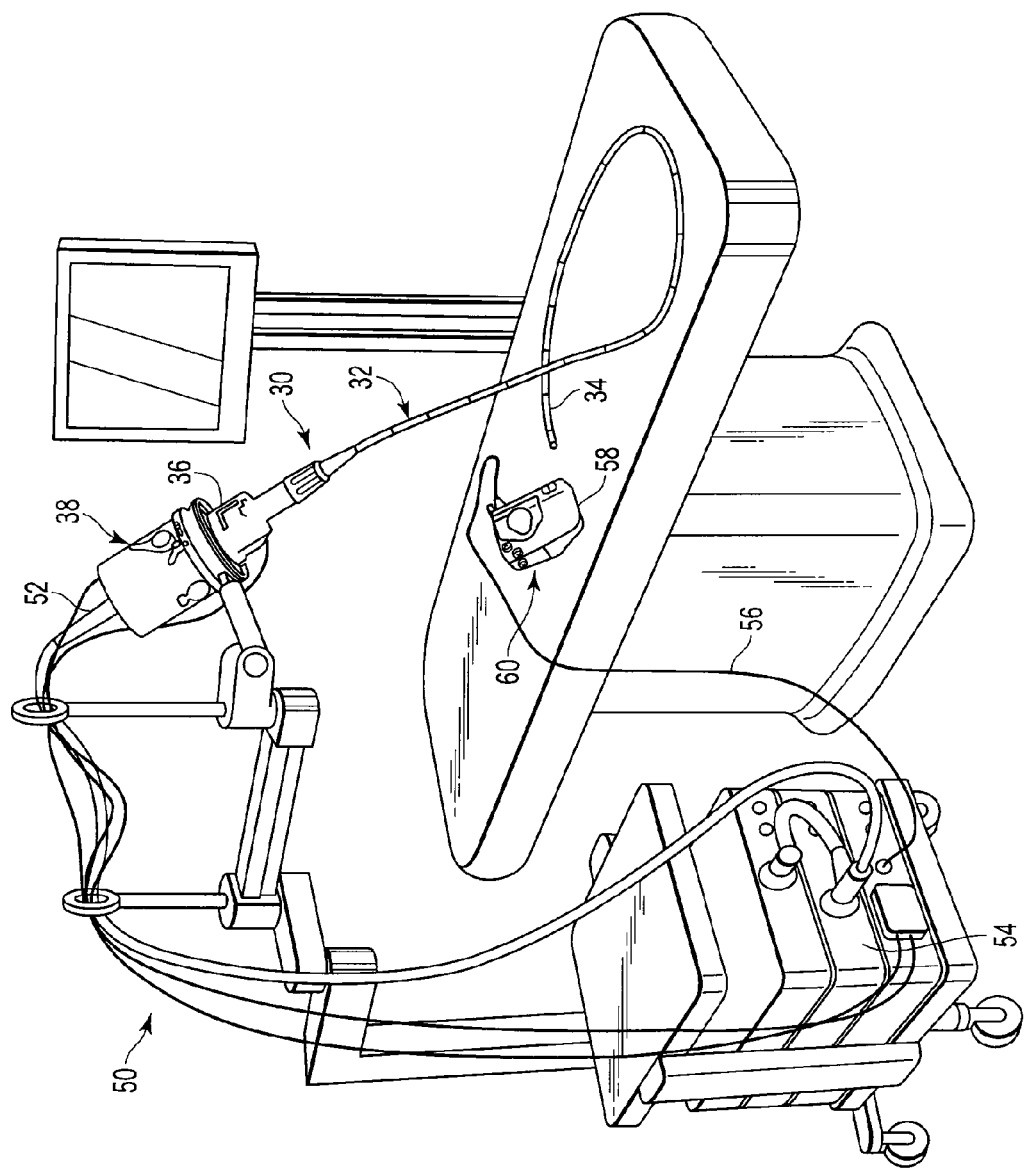
FIG. 1 is a perspective view showing an endoscope system in a first embodiment of the present invention.

Referring to FIG. 1, the schematic configuration of an endoscope system is explained.

An endoscope 30 of the endoscope system includes an elongate insertion portion 32 to be inserted into a body cavity. A bending portion 34 to be bent in four directions, that is, upward, downward, leftward and rightward is provided at the distal end of the insertion portion 32, and an insertion and removal portion 36 is provided at the proximal end of the insertion portion 32. Here, an angle mechanism is provided within the insertion and removal portion 36, and angle wires extending out of the angle mechanism are inserted through the insertion portion 32, and coupled to the distal end portion of the bending portion 34. The angle wires are moved back and forth by the angle mechanism and so the bending portion 34 is bent. A pair of angle wires for up-down bending operation and a pair of angle wires for left-right bending operation is used as the angle wires. Further, the insertion and removal portion 36 is removably inserted into a motor unit 38 as a drive unit. A motor portion as a drive portion for actuating the angle mechanism is provided within the motor unit 38. The motor unit 38 is held by a holding apparatus 50 such that the motor unit 38 is movable and fixable, and rotatable about its central axis. Moreover, the motor unit 38 is connected to a video processor 54 via a universal cord 52, and an operation portion 58 to be held and operated by an operator is connected to the video processor 54 via an electric cord 56. An operation switch 60 for bending the bending portion 34 is provided in the operation portion 58. That is, the operation switch 60 of the operation portion 58 is operated, the motor portion of the motor unit 38 is driven, the angle mechanism is actuated to move the angle wires back and forth, and so the bending portion 34 is bent in a desired direction.

Figure 2:
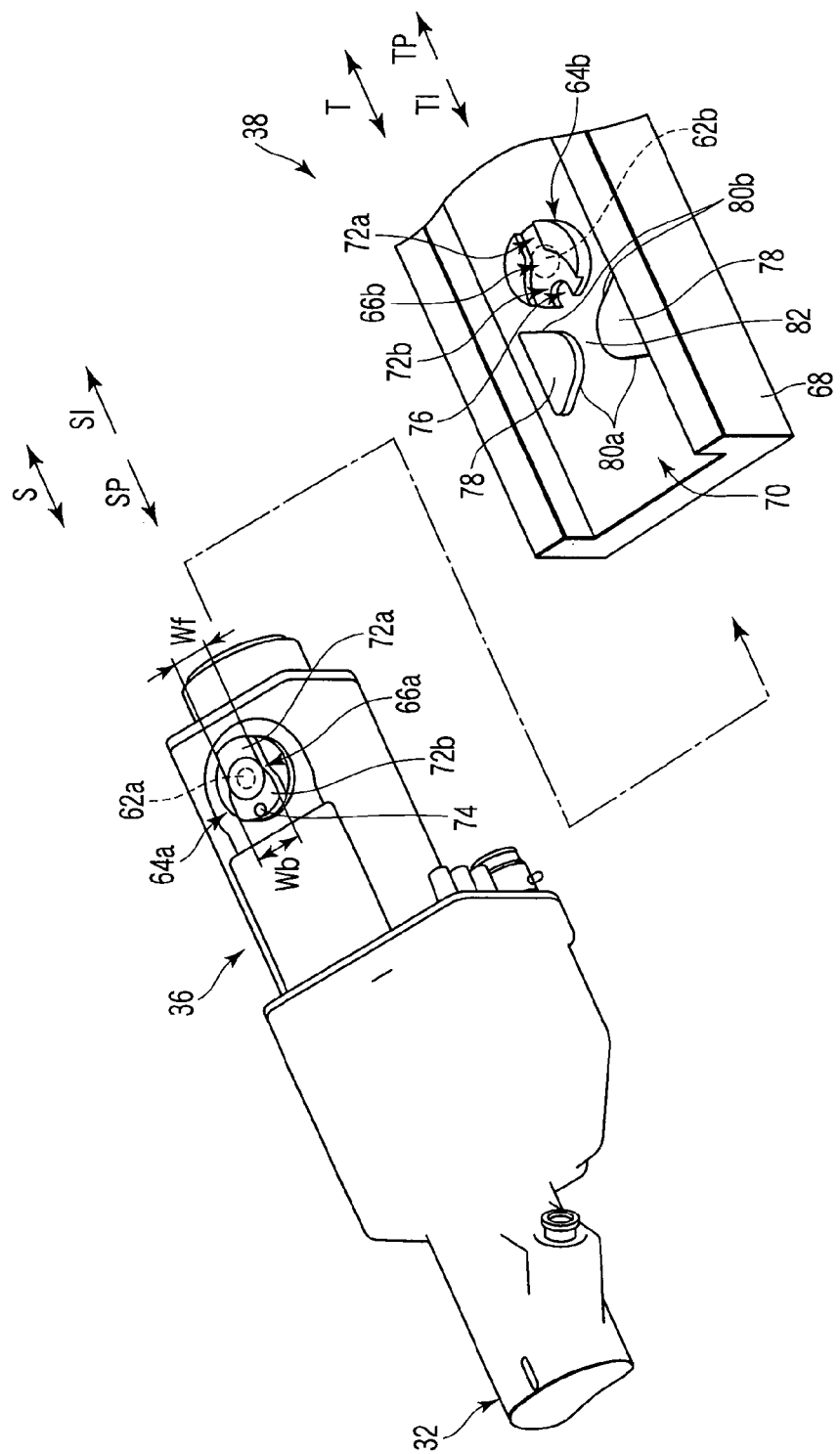
FIG. 2 is a perspective view showing a motor unit and an insertion and removal portion in the first embodiment of the present invention.

A coupling mechanism for the motor unit 38 as a second main body portion and the insertion portion 32 as a first main body portion is explained referring to FIG. 2.

The insertion and removal portion 36 of the insertion portion 32 includes a rectangular columnar shape extending in the longitudinal direction of the insertion portion 32. Driven side shaft portions 62a as first shaft portions penetrate and are disposed in one and the opposite other sidewalls of the insertion and removal portion 36 perpendicularly to these sidewalls, respectively. The proximal end of the driven side shaft portion 62a is coupled to the angle mechanism provided within the insertion and removal portion 36, and the driven side shaft portion 62a is rotatable about its central axis. When the driven side shaft portion 62a is rotated, the angle mechanism is driven, and the angle wires are moved back and forth. A circular-plate-shaped driven side coupling 64a as a first coupling is coaxially coupled to the terminal end portion of the driven side shaft portion 62a. In the terminal end face of the driven side coupling 64a, an engaging convex portion 66a as a convex engaging portion extends in the radial direction of the driven side shaft portion 62a.

On the other hand, an insertion and removal hole 70 is formed by an inner cavity of a rectangular cylindrical frame 68 of the motor unit 38 and the insertion and removal portion 36 of the insertion portion 32 is inserted to and removed from the insertion and removal hole 70 along its longitudinal direction. Driving side shaft portions 62b as second shaft portions penetrate and are disposed in one and the other sidewalls of the frame 68 to be opposite to the one and the other sidewalls of the inserted insertion and removal portion 36 perpendicularly to the sidewalls, respectively. The proximal end of the driving side shaft portion 62b is connected to the motor portion via a gear portion, and the driving side shaft portion 62b is rotatable about its central axis. A circular-plate-shaped driving side coupling 64b as a second coupling is coaxially coupled to the terminal end portion of the driving side shaft portion 62b. In the terminal end face of the driving side coupling 64b, an engaging concave portion 66b as a concave engaging portion extends in the radial direction of the driving side shaft portion 62b.

The engaging convex portion 66a of the driven side coupling 64a is slidably inserted into and removed from the engaging concave portion 66b of the driving side coupling 64b along the longitudinal direction of the engaging concave portion 66b. The engaging convex portion 66a is inserted into the engaging concave portion 66b, and so the driven side coupling 64a is coupled to the driving side coupling 64b, whereby enabling transmission of the rotation of the driving side shaft portion 62b to the driven side shaft portion 62a. On the other hand, the engaging convex portion 66a is removed from the engaging concave portion 66b, and so the driven side coupling 64a is separated from the driving side coupling 64b.

In addition, the driving side shaft portion 62b, the driving side coupling 64b, the driven side coupling 64a and the driven side shaft portion 62a on one side are used for the up-down bending operation, those on the other side are used for the left-right bending operation, and both of those have the same configuration.

Furthermore, the hardness of the driving side coupling 64b is higher than the hardness of the driven side coupling 64a. For example, the driving side coupling 64b is formed of steel with a high hardness, and the driven side coupling 64a is formed of steel with a low hardness. Moreover, the couplings 64b and 64a may be different from each other in material and so in hardness, for example, the driving side coupling 64b may be formed of stainless steel and the driven side coupling 64a may be formed of aluminum. Further, the couplings 64b and 64a made of the same material are different in surface treatment and so in hardness, for example, the driving side coupling 64b may be formed of stainless steel with nitrided surface and the driven side coupling 64a may be formed of stainless steel with untreated surface.

Referring to FIGS. 2 and 3, a guide mechanism is explained to guide the engaging convex portion 66a of the driven side coupling 64a when the insertion portion 32 is inserted into and removed from the motor unit 38.

As described above, the insertion and removal portion 36 of the insertion portion 32 is inserted into and removed from the insertion and removal hole 70 of the motor unit 38 along its longitudinal direction. Here, the longitudinal direction, longitudinal direction toward the rear side and longitudinal direction toward the distal side of the insertion and removal portion 36 are defined as an attachment and detachment direction S, attachment direction SI and detachment direction SP of the insertion and removal portion 36, respectively. Moreover, the longitudinal direction, longitudinal direction toward the distal side and longitudinal direction toward the rear side of the motor unit 38 are defined as an attachment and detachment direction T, attachment direction TI and detachment direction TP of the motor unit 38, respectively.

The engaging convex portion 66a of the driven side coupling 64a and the engaging concave portion 66b of the driving side coupling 64b include basic positions where the longitudinal directions of the engaging convex portion 66a and the engaging concave portion 66b correspond to the attachment and detachment directions S and T of the insertion and removal portion 36 and the motor unit 38 respectively and the engaging convex portion 66a and the engaging concave portion 66b are insertable into and removable from each other. The amount of bending of the bending portion 34 is set to be zero when the engaging convex portion 66a is at the basic position, and the rotation of the engaging convex portion 66a in one or the other direction causes the bending portion 34 to bend upward or downward, or, rightward or leftward. Moreover, the amount of rotation of the motor portion of the motor unit 38 is set to be zero when the engaging concave portion 66b is at the basic position.

The engaging convex portion 66a of the driven side coupling 64a extends over the entire diameter of the driven side coupling 64a. In the engaging convex portion 66a, a width Wf of the side located on the distal end side of the attachment direction SI of the insertion and removal portion 36 when the engaging convex portion 66a is at the basic position is smaller than a width Wb of the side located on the rear end side, and a narrow portion 72a and a wide portion 72b are formed. On the other hand, the engaging concave portion 66b of the driving side coupling 64b extends over the entire diameter of the driving side coupling 64b and includes a shape corresponding to the shape of the engaging convex portion 66a, and so a narrow portion 72a and a wide portion 72b are also formed in the engaging concave portion 66b.

In the terminal end face of the engaging convex portion 66a of the driven side coupling 64a, a guide pin 74 as a guide portion protrudes from an end portion located on the rear end side of the attachment direction SI (distal end side of the detachment direction SP) of the insertion and removal portion 36 when the engaging convex portion 66a is at the basic position. On the other hand, in the bottom surface of the engaging concave portion 66b of the driving side coupling 64b, a concave containing portion 76 for containing the guide pin 74 extends from the outer peripheral surface of the driving side coupling 64b toward its center at an end portion located on the distal end side of the attachment direction TI (rear end side of the detachment direction TP) of the motor unit 38 when the engaging concave portion 66*b* is at the basic position.

A pair of guide members 78 protrudes from the inner wall of the motor unit 38 and is disposed on the distal end side of the attachment direction TI (rear end side of the detachment direction TP) of the motor unit 38 with respect to the engaging concave portion 66*b* of the driving side coupling 64*b*, and the pair of guide members 78 are in line symmetry to each other with respect to the central line of the engaging concave portion 66*b* located at the basic position. The terminal end faces of the guide members 78 are disposed closer to the proximal side than the bottom surface of the engaging concave portion 66*b* and so the guide members 78 don't interfere with the engaging convex portion 66*a*. In the pair of guide members 78, a pair of insertion guide surfaces 80*a* as guide receiving portions is formed on the distal end side of the attachment direction TI of the motor unit 38 respectively, which inclines from the distal end side to rear end side to approach the central line. On the other hand, in the pair of guide members 78, a pair of removal guide surfaces 80*b* as guide receiving portions is formed on the distal end side of the detachment direction TP of the motor unit 38, which inclines from the distal end side to rear end side to approach the central line. In addition, the distance between the outer peripheral surface of the driving side coupling 64*b* and the removal guide surface 80*b* is greater than the diameter of the guide pin 74. Formed between the insertion guide surfaces 80*a* and the removal guide surfaces 80*b* is a gap portion 82 having a width slightly greater than the diameter of the guide pin 74 between the pair of guide members 78.

Next will be described the coupling and separation of the driving side coupling 64*b* and the driven side coupling 64*a* when the insertion portion 32 is inserted into and removed from the motor unit 38.

The insertion of the insertion and removal portion 36 of the insertion portion 32 into the motor unit 38 is explained by referring to FIG. 4.

Before insertion, the rotation amount of the motor portion of the motor unit 38 is substantially zero, and the engaging concave portion 66*b* of the driving side coupling 64*b* is substantially at the basic position. On the other hand, the bending portion 34 of the insertion portion 32 is rarely completely linear and is generally slightly bent. The engaging convex portion 66*a* of the driven side coupling 64*a* is located at a position rotated by a slight angle from the basic position in accordance with the bending amount of the bending portion 34. Moreover, even when the bending portion 34 is completely linear, the engaging convex portion 66*a* may not be completely disposed at the basic position due to component accuracy. As the insertion and removal portion 36 of the insertion portion 32 is inserted into the motor unit 38, the engaging convex portion 66*a* is inserted without interfering with the guide members 78, and the guide pin 74 protruding from the engaging convex portion 66*a* contacts the insertion guide surface 80*a*. As the insertion and removal portion 36 is further inserted into the motor unit 38, the guide pin 74 slides on and is guided by the insertion guide surface 80*a*, the driven side coupling 64*a* is rotated, and so the engaging convex portion 66*a* is rotated into the basic position. Here, the narrow portion 72*a* of the engaging convex portion 66*a* is disposed on the distal end side of the attachment direction SI of the insertion and removal portion 36 and the wide portion 72*h* of the engaging concave portion 66*b* is disposed on the distal end side of the attachment direction TI of the motor unit 38, and so the engaging convex portion 66*a* is inserted into the engaging concave portion 66*b* before the engaging convex portion 66*a* is disposed at the basic position. As the insertion and removal portion 36 is further inserted into the motor unit 38, the engaging convex portion 66*a* is located at the basic position at the point where the guide pin 74 has reached the gap portion 82 between the pair of guide members 78, and the engaging convex portion 66*a* is inserted into the engaging concave portion 66*b* along the longitudinal direction of the engaging concave portion 66*b*. When the engaging convex portion 66*a* is completely inserted into the engaging concave portion 66*b*, the guide pin 74 is inserted and contained in the containing portion 76.

The removal of the insertion and removal portion 36 of the insertion portion 32 from the motor unit 38 is explained by referring to FIG. 5.

Before removal, although the rotation amount of the motor portion of the motor unit 38 is operated to be zero, there may remain a slight amount of rotation. In this case, the engaging concave portion 66*b* of the driving side coupling 64*b* of the motor unit 38 and the engaging convex portion 66*a* of the driven side coupling 64*a* of the insertion portion 32 are located at positions rotated by a slight angle from the basic positions in accordance with the rotation amount of the motor portion of the motor unit 38. Moreover, even when the rotation amount of the motor portion is zero, the engaging concave portion 66*b* and the engaging convex portion 66*a* may not be completely disposed at the basic positions due to control accuracy or component accuracy. As the insertion and removal portion 36 of the insertion portion 32 is removed from the motor unit 38, the engaging convex portion 66*a* is removed from the engaging concave portion 66*b*, and the guide pin 74 of the engaging convex portion 66*a* contacts the removal guide surface 80*b*. As the insertion and removal portion 36 is further removed from the motor unit 38, the guide pin 74 slides on and is guided by the removal guide surface 80*b*, the driven side coupling 64*a* is rotated, and so the engaging convex portion 66*a* is rotated into the basic position. Here, since the distance between the removal guide surface 80*b* and the outer peripheral surface of the driving side coupling 64*b* is greater than the diameter of the guide pin 74, the guide pin 74 can move in a space 83 therebetween along the removal guide surface 80*b*. As the insertion and removal portion 36 is further removed from the motor unit 38, the engaging convex portion 66*a* is located at the basic position at the point where the guide pin 74 has reached the gap portion 82 between the pair of guide members 78, and the engaging convex portion 66*a* is then removed from the engaging concave portion 66*b*. The rotation of the engaging convex portion 66*a* to the basic position causes the engaging concave portion 66*b* to be also rotated to the basic position. Thus, after the insertion and removal portion 36 has been removed from the motor unit 38, the rotation amount of the motor portion of the motor unit 38 is substantially zero, and the bending portion 34 of the insertion portion 32 is substantially linear.

Therefore, the attachment and detachment mechanism of the present embodiment provides the following effects:

In the insertion and removal mechanism of the present embodiment, when the insertion and removal portion 36 of the insertion portion 32 is inserted into and removed from the motor unit 38, the engaging convex portion 66*a* of the driven side coupling 64*a* of the insertion and removal portion 36 is guided to the basic position corresponding to the attachment and detachment direction and suitable for insertion and removal. Thus, in the insertion, the engaging convex portion 66*a* is automatically inserted into the engaging concave portion 66*b* by simply disposing the engaging concave portion 66*b* of the driving side coupling 64*b* of the motor unit 38 substantially at the basic position. In the removal, the engaging concave portion 66b is also guided to the basic position in conjunction with the engaging convex portion 66a. Then, the insertion and removal of the engaging convex portion 66a with respect to the engaging concave portion 66b can be easily and smoothly carried out. Therefore, the insertion and removal of the insertion and removal portion 36 with respect to the motor unit 38 can be easily and smoothly carried out.

Furthermore, the narrow portion 72a of the engaging convex portion 66a is located on the distal end side of the attachment direction SI of the insertion and removal portion 36 and the wide portion 72b of the engaging concave portion 66b is located on the distal end side of the attachment direction TI of the motor unit 38, and so even when the engaging convex portion 66a is displaced from the basic position, the engaging convex portion 66a can be inserted into the engaging concave portion 66b.

Moreover, in the engaging convex portion 66a, the guide pin 74 is provided on the side located on the rear end side of the attachment direction SI of the insertion and removal portion 36, and so the guide pin 74 may be guided by the insertion guide surface 80a after the driven side coupling 64a has sufficiently approached the driving side coupling 64b. Thus, the insertion guide surface 80a can be disposed in sufficient proximity to the engaging concave portion 66b, and the entire length of the insertion and removal mechanism in the attachment and detachment direction can be reduced.

Figure 6:
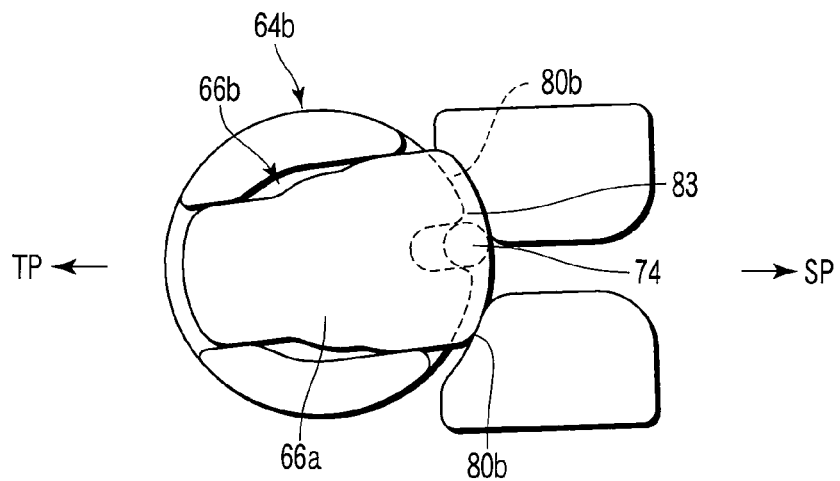
FIG. 6 is a schematic diagram showing the removal of the insertion and removal mechanism in a comparative example of the first embodiment of the present invention.

In addition, since the distance between the outer peripheral surface of the driving side coupling 64b and the removal guide surface 80b is greater than the diameter of the guide pin 74, the guide pin 74 can move in the space 83 between the outer peripheral surface of the driving side coupling 64b and the removal guide surfaces 80b along the removal guide surface 80b when the insertion and removal portion 36 is removed from the motor unit 38, which prevents the movement of the guide pin 74 from being hampered by the removal guide surfaces 80b and thus the removal of the engaging convex portion 66a from the engaging concave portion 66b from being hampered. That is, referring to FIG. 6, in the case where the distance between the removal guide surfaces 80b and the outer peripheral surface of the driving side coupling 64b is smaller than the diameter of the guide pin 74, the guide pin 74 cannot move in the space 83 therebetween, and the engaging convex portion 66a cannot be removed from the engaging concave portion 66b.

Still further, in the endoscope system, various insertion portions 32 adapted to cases are used with respect to one motor unit 38 and the driving side coupling 64b is used more frequently than the driven side coupling 64a. However, as the hardness of the driving side coupling 64b is higher than the hardness of the driven side coupling 64a, the life of the whole endoscope is extended.

FIGS. 7 to 10 show a second embodiment of the present invention.

Figure 7:
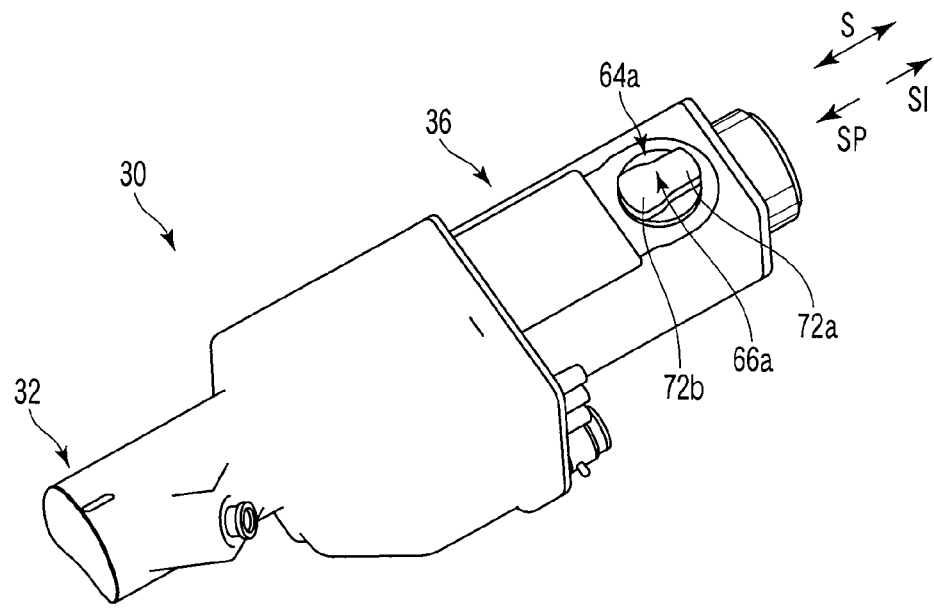
FIG. 7 is a perspective view showing an insertion and removal portion in a second embodiment of the present invention.
Figure 8:
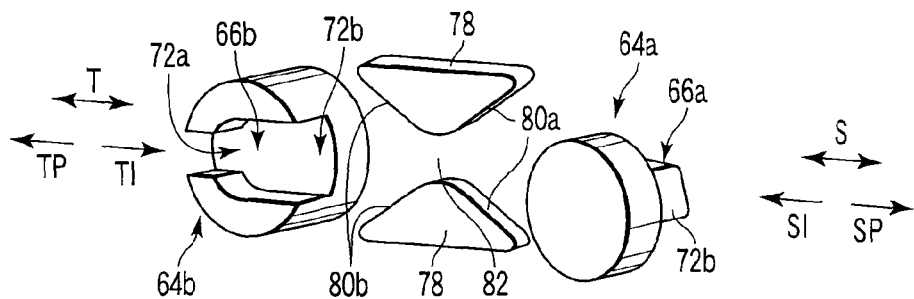
FIG. 8 is a schematic diagram showing an insertion and removal mechanism in the second embodiment of the present invention.

Referring to FIGS. 7 and 8, the engaging convex portion 66a and the engaging concave portion 66b of the present embodiment have shapes similar to those of the engaging convex portion 66a and the engaging concave portion 66b of the first embodiment. However, no guide pin 74 and containing portion 76 are provided in the engaging convex portion 66a and the engaging concave portion 66b, and the engaging convex portion 66a itself forms the guide portion to be guided by insertion guide surfaces 80a and removal guide surfaces 80b. That is, the terminal end face of the guide member 78 is disposed between the bottom surface and an opening surface of the engaging concave portion 66b, and so the guide member 78 only interferes with the engaging convex portion 66a.

Moreover, formed between the insertion guide surfaces 80a and the removal guide surfaces 80b is the gap portion 82 including a width slightly greater than the wide portion 72b of the engaging convex portion 66a between the pair of guide members 78. In addition, the space 83 is formed between the outer peripheral surface of the driving side coupling 64b and the removal guide surfaces 80b such that the end portion side of the wide portion 72b of the engaging convex portion 66a disposed on the distal end side of the detachment direction SP of the insertion and removal portion 36 can move without being disturbed by the removal guide surfaces 80b when the engaging convex portion 66a is removed from the engaging concave portion 66b.

Figure 9:
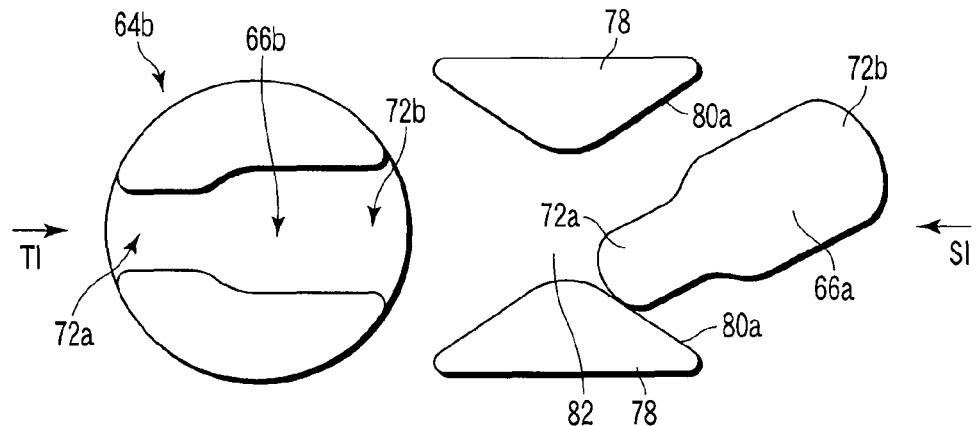
FIG. 9 is a schematic diagram showing the insertion of the insertion and removal mechanism in the second embodiment of the present invention.

Referring to FIG. 9, when the insertion and removal portion 36 of the insertion portion 32 is inserted into the motor unit 38, the narrow portion 72a of the engaging convex portion 66a disposed on the distal end side of the attachment direction SI of the insertion and removal portion 36 is guided by the insertion guide surface 80a, and so the engaging convex portion 66a is rotated into the basic position. Here, since the gap portion 82 between the pair of guide members 78 has a width slightly greater than the wide portion 72b of the engaging convex portion 66a, the narrow portion 72a of the engaging convex portion 66a is inserted into the gap portion 82 before the engaging convex portion 66a is completely disposed at the basic position. Thus, when the distance between the gap portion 82 and the driving side coupling 64b is shorter than the length of the narrow portion 72a in the attachment and detachment direction T of the motor unit 38, the engaging convex portion 66a is inserted into the engaging concave portion 66b before the engaging convex portion 66a is completely disposed at the basic position, as in the first embodiment.

Figure 10:
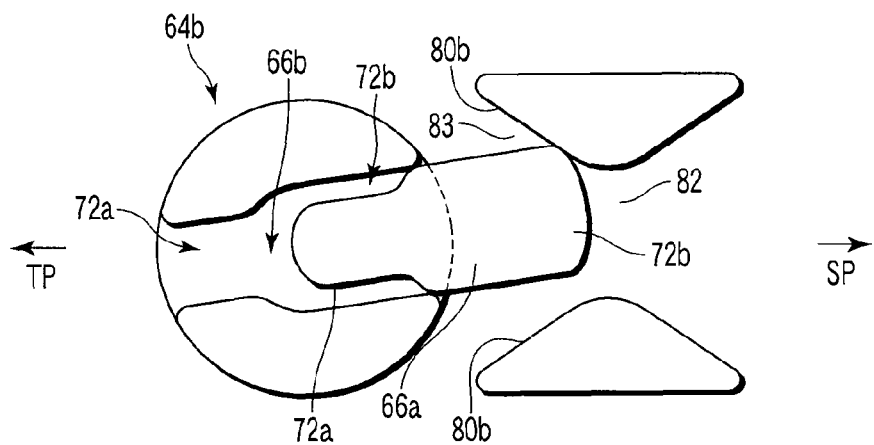
FIG. 10 is a schematic diagram showing the removal of the insertion and removal mechanism in the second embodiment of the present invention.

Referring to FIG. 10, when the insertion and removal portion 36 of the insertion portion 32 is removed from the motor unit 38, the wide portion 72b of the engaging convex portion 66a disposed on the distal end side of the detachment direction SP of the insertion and removal portion 36 contacts the removal guide surface 80b, and the wide portion 72b swings in the space 83 between the outer peripheral surface of the driving side coupling 64b and the removal guide surfaces 80b and is guided by the removal guide surface 80b, and so the engaging convex portion 66a is rotated into the basic position.

Therefore, the insertion and removal mechanism of the present embodiment provides the following effects:

In the insertion and removal mechanism of the present embodiment, the engaging convex portion 66a itself is guided by the insertion guide surfaces 80a and the removal guide surfaces 80b, and no additional members or processing are needed for guiding the engaging convex portion 66a, and so the configuration of the insertion and removal mechanism is simplified, and simpler manufacture, reduced occurrence of failures and reduced costs are achieved.

FIG. 11 shows a first modification of the second embodiment of the present invention.

In the present modification, in the terminal end face of the driven side coupling 64a, a circular columnar small-diameter protrusion 67a (outside diameter Wf) and a circular columnar large-diameter protrusion 67b (outside diameter Wb) greater than the small-diameter protrusion 67a in diameter protrude from both diametrical ends of this terminal end face, respectively. The engaging convex portion 66a is formed by the small-diameter protrusion 67a and the large-diameter protrusion 67b. Thus, the engaging convex portion extending in the radial direction of the shaft portion is not limited to the continuous engaging convex portion. When the engaging convex portion 66a is at the basic position, the small-diameter protrusion 67a is disposed on the distal end side of the attachment direction SI of the insertion and removal portion 36, and the large-diameter protrusion 67b is disposed on the rear end side. The operation of the insertion and removal mechanism of the present modification in the insertion and removal is similar to that in the second embodiment.

FIGS. 12 to 15 show a second modification of the second embodiment of the present invention.

Referring to FIGS. 12 and 13, in the present modification, a length Lf of the narrow portion 72a is sufficiently smaller than a length Lb of a wide portion 72b in the longitudinal direction of the engaging convex portion 66a.

Referring to FIG. 14, the length of the narrow portion 72a disposed on the distal end side of the attachment direction of the insertion and removal portion 36 is sufficiently short. Thus, when the insertion and removal portion 36 of the insertion portion 32 is inserted into the motor unit 38, the narrow portion 72a does not contact insertion guide surfaces 80a, and the wide portion 72b disposed on the proximal side of the attachment direction SI of the insertion and removal portion 36 contacts and is guided by the insertion guide surface 80a, and so the engaging convex portion 66a is rotated into the basic position. That is, in the present modification, the guide portion is formed by the wide portion 72b, and, as in the first embodiment, the guide portion is formed in the engaging convex portion 66a on the side located on the rear end side of the attachment direction SI of the insertion and removal portion 36.

Referring to FIG. 15, the operation of the insertion and removal mechanism in removal is similar to that in the second embodiment.

FIGS. 16 and 17 show a third embodiment of the present invention.

Referring to FIGS. 16 and 17, a drip-proof structure of the coupling mechanism is explained.

As described above, an engaging concave portion 66b extends over the entire radial direction of the driving side coupling 64b in the terminal end face of the driving side coupling 64b. In the bottom surface of the engaging concave portion 66b, a holding concave portion 90 extends in the radial direction of the driving side coupling 64b perpendicularly to the longitudinal direction of the engaging concave portion 66b. A cover 92 covers the entire bottom surface of the engaging concave portion 66b, and a holding portion 94 is formed between the cover 92 and the holding concave portion 90. In the holding concave portion 90, an insertion groove 88 extends in the diametrical direction of the driving side coupling 64b along the longitudinal direction of the holding concave portion 90. The insertion groove 88 penetrates between the holding concave portion 90 and a slide concave portion 86 extending on the proximal surface of the driving side coupling 64b. The slide concave portion 86 extends in the diametrical direction of the driving side coupling 64b perpendicularly to the longitudinal direction of the engaging concave portion 66b.

On the other hand, the driving side shaft portion 62b is supported on the frame 68 of the motor unit 38 rotatably about its central axis, as described above. A slide convex portion 84 extends in the diametrical direction of the driving side shaft portion 62b in the terminal surface of the driving side shaft portion 62b. The longitudinal direction of the slide convex portion 84 corresponds to the longitudinal direction of the slide concave portion 86, and the slide convex portion 84 is clearance-fitted into the slide concave portion 86 slidably along the longitudinal direction of the slide concave portion 86. The longitudinal length of the slide concave portion 86 is what given by adding the doubled allowable eccentric length of the driving side coupling 64b with respect to the central axis of the driving side shaft portion 62b to the longitudinal length of the slide convex portion 84.

A holding hole 96 perforate axially into the terminal end face of the slide convex portion 84. The proximal side of the rod-like portion of a holding member 98 is axially slidably inserted into the holding hole 96. The terminal side of the rod-like portion of the holding member 98 is inserted through the insertion groove 88 from the slide concave portion 86 to the holding concave portion 90. The rod-like portion is slidable along the longitudinal direction of the insertion groove 88 without disturbing the sliding of the slide convex portion 84 in the slide concave portion 86. A plate-like portion is coupled to the terminal end face of the rod-like portion of the holding member 98 perpendicularly to the rod-like portion. This plate-like portion is held by the holding portion 94 between the holding concave portion 90 and the cover 92, and functions to prevent the driving side coupling 64b coming off. Moreover, the plate-like portion is slidable along the longitudinal direction of the holding portion 94 without disturbing the sliding of the slide convex portion 84 in the slide concave portion 86.

An annular seal groove 100 about the driving side shaft portion 62b extends in the frame 68 of the motor unit 38 opposite to the driving side coupling 64b. An annular seal member 102 of a surface-contact type is fitted into the seal groove 100. That is, the seal member 102 is compressed between the frame 68 and the proximal end surface of the driving side coupling 64b, and is in surface contact with the frame 68 and the proximal surface of the driving side coupling 64b, and so the seal member 102 exerts an axially outward repulsion on the proximal surface of the driving side coupling 64b. For example, an O-ring or a V-ring is used as the seal member 102. In addition, the inside diameter of the seal member 102 is greater than what given by adding the doubled allowable eccentric length of the driving side coupling 64b to the longitudinal length of the slide convex portion 84 of the driving side shaft portion 62b, and the outside diameter of the seal member 102 is smaller than what given by subtracting the doubled allowable eccentric length of the driving side coupling 64b from the longitudinal length of the driving side coupling 64b.

Therefore, the insertion and removal mechanism of the present embodiment provides the following effects:

In the insertion and removal mechanism of the present embodiment, the seal member 102 is provided between the driving side coupling 64b and the frame 68, and so an axial length from the frame 68 to the terminal end face of the driving side coupling 64b can be sufficiently small, in particular, as compared with a case where the seal member 102 is provided between the driving side shaft portion 62b and the frame 68. Moreover, especially, since the slide convex portion 84 of the driving side shaft portion 62b is clearance-fitted into the slide concave portion 86 of the driving side coupling 64b, the driving side coupling 64b tends to rock about the longitudinal axis of the slide convex portion 84. However, as the seal member 102 exerts the axially outward repulsion on the proximal end surface of the driving side coupling 64b, the rocking is suppressed, and the driving side coupling 64b is stably rotated.

FIG. 18 shows a fourth embodiment of the present invention.

In a driving side coupling 64b of the present embodiment, the seal groove 100 extends over the entire outer peripheral surface of its proximal end, and the annular seal member 102 is fitted into and joined to the seal groove 100. The function of the seal member 102 is similar to that in the third embodiment. Owing to such a configuration, an axial length from the frame 68 to the terminal surface of the driving side coupling 64b can be further reduced.

FIGS. 19 to 24 show a referential embodiment of the present invention.

A driving mechanism of a motor unit 38 is explained with reference to FIGS. 19 to 24.

Figure 19:
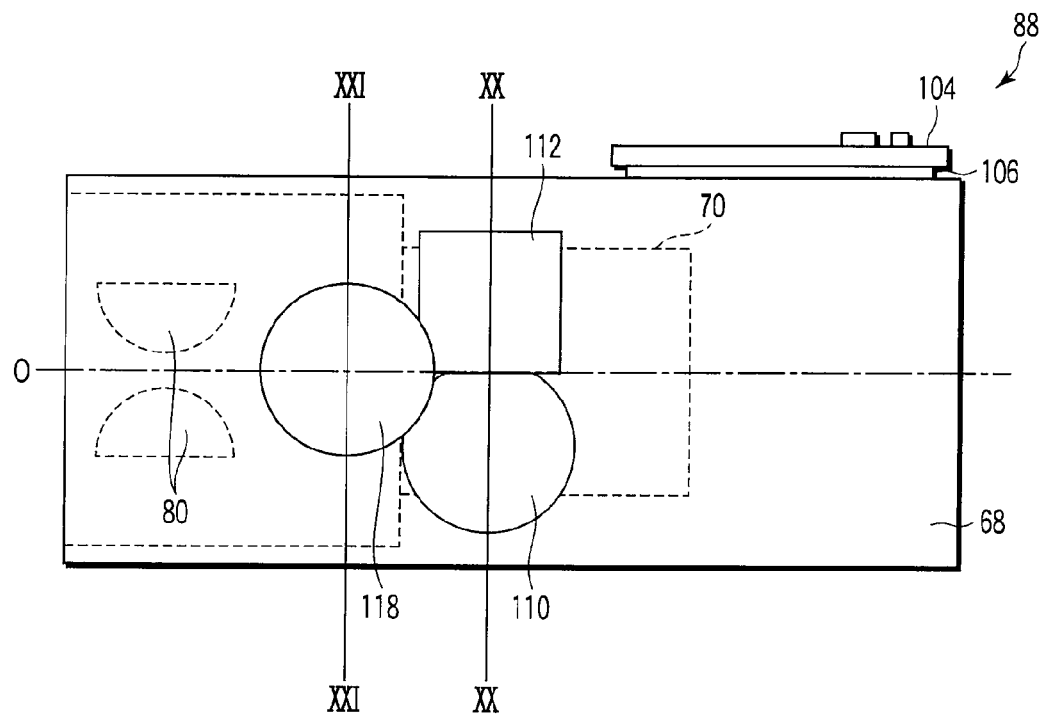
FIG. 19 is a diagram showing the internal structure of a motor unit in a referential embodiment of the present invention.
Figure 20:
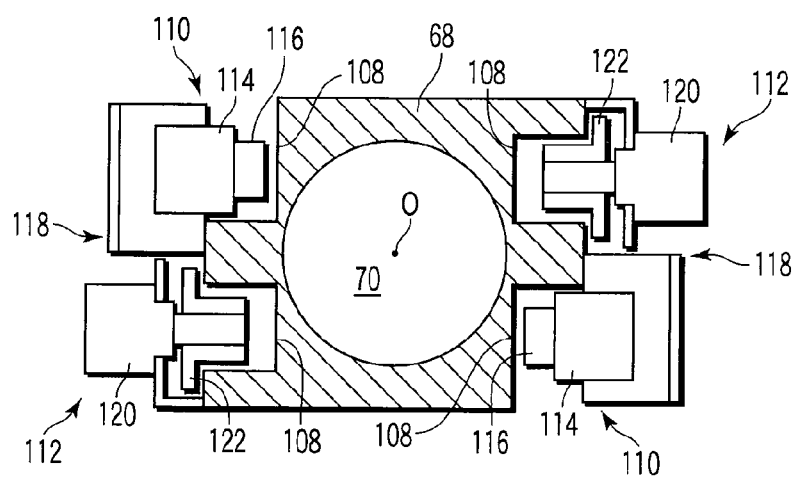
FIG. 20 is a sectional view showing the motor unit in the referential embodiment of the present invention cut along the XX-XX line in FIG. 19.

Referring to FIGS. 19 and 20, a substrate 104 on which various elements are mounted is provided on the rear side of the motor unit 38. The distal end of the substrate 104 is thermally connected to the frame 68 via heat-radiating rubber 106, and the frame 68 functions as a heat-radiating member of the substrate 104. Further, the frame 68 has a shape such that a circular columnar insertion and removal hole 70 is coaxially formed in a rectangular parallelepiped extending in the attachment and detachment direction of the motor unit 38, and cutout-shaped containing spaces 108 are formed at four corners of the frame 68 in a cross section perpendicular to the longitudinal direction of the frame 68. Using a pair of containing spaces 108 symmetric with respect to a central axis 0, a motor portion 110 for up-down bending operation and a motor portion 110 for left-right bending operation are provided in rotational symmetric with respect to the central axis O of the frame 68. Using another pair of containing spaces 108, a sensor portion 112 for detecting the amount of up-down bending operation and a sensor portion 112 for detecting the amount of left-right bending operation are provided in rotational symmetry with respect to the central axis O of the frame 68. Further, the motor portion 110 includes a motor 114 and an encoder 116. The motor 114 is connected to a driving side coupling 64b via a gear portion 118, and a sensor gear 122 of the gear portion 118 is coupled to a sensor 120 of the sensor portion 112. The gear portion 118 for up-down bending operation and the gear portion 118 for left-right bending operation are provided in rotational symmetry to each other with respect to the central axis O of the frame 68.

Referring to FIG. 21, the motor 114 of the motor portion 110 is connected to the driving side coupling 64b via the gear portion 118. On the side of the driving side coupling 64b of the gear portion 118, a gear shaft 128 supported by a gear flange 126 is rotated by a spur gear 124.

Figure 23:
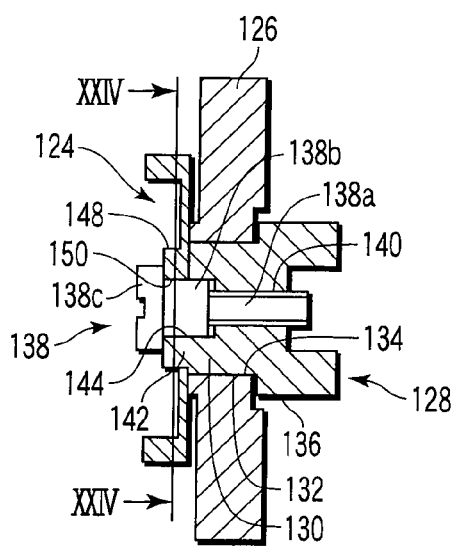
FIG. 23 is a sectional view showing the support structure of the gear shaft in the referential embodiment of the present invention cut along the XXIII-XXIII line in FIG. 24.
Figure 24:
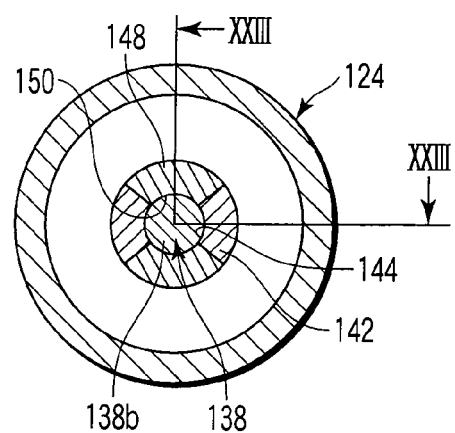
FIG. 24 is a sectional view showing the support structure of the gear shaft in the referential embodiment of the present invention cut along the XXIV-XXIV line in FIG. 23.

Referring to FIGS. 22 to 24, a circular columnar bearing bore 130 penetrate the gear flange 126, and a bearing surface 132 is formed by the inner peripheral surface of the gear flange 126, defining the bearing bore 130.

The circular columnar gear shaft 128 is coaxially inserted through the bearing bore 130 rotatably about its central axis, and a sliding surface 134 to slide over the bearing surface 132 is formed by the outer peripheral surface of the gear shaft 128. A flange 136 for preventing the fall of the gear shaft 128 into the bearing bore 130 extends over the whole circumference at the terminal end side of the gear shaft 128. In the gear shaft 128, a screw hole 140 through which a screw portion 138a on the terminal side of a fixing screw 138 is inserted penetrates the gear shaft 128 along its central axis. A pair of gear shaft dog clutches 142 projects from the proximal surface of the gear shaft 128 symmetrically with respect to the central axis of the gear shaft 128, and the cross section of the gear shaft dog clutch 142 perpendicular to the central axis forms a fan shape coaxial with the central axis of the gear shaft 128. A gear shaft centering surface 144 into which a centering portion 138b in the middle part of the fixing screw 138 is fitted is formed by an inner arc surface of the gear shaft dog clutch 142.

On the other hand, a pair of fitting holes 146 penetrate the spur gear 124 symmetrically with respect to the central axis of the spur gear 124, and the cross section of the fitting hole 146 perpendicular to the central axis has the same shape as that of the cross section of the gear shaft dog clutch 142 and forms a fan shape coaxial with the central axis of the spur gear 124. Spur gear dog clutches 148 protrudes between a pair of fitting holes 146 symmetrically with respect to the central axis, and the cross section of the spur gear dog clutch 148 perpendicular to the central axis of the spur gear 124 forms a fan shape coaxial with the central axis of the spur gear 124. A spur gear shaft centering surface 150 into which the outer peripheral surface of the centering portion 138b of the fixing screw 138 is fitted is also formed by an inner arc surface of the spur gear dog clutch 148.

The gear shaft dog clutch 142 is fitted into the fitting hole 146 of the spur gear 124, and the gear shaft dog clutch 142 and the spur gear dog clutch 148 are engaged with each other.

A head 138c of the fixing screw 138 is engaged onto the proximal surface of the spur gear dog clutch 148, and the centering portion 138b of the fixing screw 138 is fitted into the spur gear shaft centering surface 150 and the gear shaft centering surface 144. The screw portion 138a of the fixing screw 138 is inserted through the screw hole 140 of the gear shaft 128, and protruded from the gear shaft 128.

Therefore, the motor unit 38 of the referential embodiment provides the following effects:

In the motor unit 38 of the referential embodiment, the cutout-shaped containing spaces 108 are formed at four corners in the cross section perpendicular to the longitudinal direction of the frame 68, thereby enabling the effective utilization of space and the size reduction of the motor unit 38.

Furthermore, the driving mechanism for up-down bending operation and the driving mechanism for left-right bending operation are provided in rotational symmetry to each other with respect to the central axis O of the frame 68, and so the center of gravity of the motor unit 38 is disposed on the central axis. In the case where the center of gravity of the motor unit 38 is off the central axis, stable operation is difficult when the insertion portion 32 attached to the motor unit 38 is rotated, but such a situation is prevented in the referential embodiment.

Still further, the flange 136 for preventing the fall of the gear shaft 128 into the bearing bore 130 is formed in the gear shaft 128, and so, even when an external force toward the proximal side is applied to the gear shaft 128, the gear shaft 128 does not fall into the bearing bore 130 to press the spur gear 124 toward the proximal side, thereby preventing the spur gear 124 from interfering with other gears to cause rotation failure. Especially, in the case where the gear shaft 128 and the spur gear 124 are formed as one component, the spur gear 124 tends to be moved toward the proximal side, and so the effects of the flange 136 are obviously displayed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An endoscope comprising:
a drive unit configured to form one of first and second main body portions to be attached to and detached from each other;
an insertion portion including a bendable bending portion, which is configured to form the other of the first and second main body portions;

a first shaft portion including a terminal end portion and a proximal end portion, the proximal end portion of the first shaft portion being supported by the first main body portion rotatably about a central axis of the first shaft portion;

a first coupling provided at the terminal end portion of the first shaft portion;

a convex engaging portion which is provided in the first coupling and which includes a distal end and a base end and extends from the distal end to the base end in a radial direction of the first shaft portion;

a second shaft portion including a terminal end portion and a proximal end portion, the proximal end portion of the second shaft portion being supported by the second main body portion rotatably about a central axis of the second shaft portion;

a second coupling provided at the terminal end portion of the second shaft portion;

a concave engaging portion which is provided in the second coupling and extends in a radial direction of the second shaft portion, wherein the convex and concave engaging portions, before engaging each other, include basic positions where the longitudinal directions of the convex and concave engaging portions correspond to an attachment and detachment direction of the first and second main body portions and, wherein the convex and concave engaging portions are insertable into and removable from each other, the convex engaging portion is being configured to be slidably inserted into and removed from the concave engaging portion along the longitudinal direction of the concave engaging portion;

a drive portion configured to rotate one of the first and second shaft portions;

a bending mechanism configured to bend the bending portion by a rotation of the other of the first and second shaft portions, and a pair of guide members which is provided on the second main body portion and configured to provide a guide so as to locate the convex and concave engaging portions on the basic positions and which includes a pair of insert guide surfaces opposed to each other and configured to slide the convex engaging portion and a pair of remove guide surfaces opposed to each other and also configured to slide the base portion of the convex engaging portion, wherein;

the pair of insert guide surfaces are formed so that a distance between the pair of insert guide surfaces becomes smaller towards a direction in which the convex engaging portion is attached form the basic position to the concave engaging portion, and the pair of remove guide surfaces are formed so that a distance between the pair of remove guide surfaces becomes smaller towards a direction in which the convex engaging portion engaged with the concave engaging portion is removed to the basic position.

2. The endoscope according to claim 1, wherein the convex engaging portion includes a guide portion which is configured to slide to the guide members.

3. The endoscope according to claim 1, wherein the convex engaging portion includes a wide portion being larger in width than the distal end of the convex engaging portion and a narrow portion being narrower in width than the base end of the convex engaging portion.

4. The endoscope according to claim 2, wherein the guide portion is formed on the base end of the convex engaging portion.

5. The endoscope according to claim 2, wherein a moveable gap is formed between the pair of guide members and the guide portion.

6. The endoscope according to claim 2, wherein
one coupling between the first and second coupling is slidable in a radial direction with respect to the one shaft portion of the first and second shaft portions provided with the one coupling, and
the endoscope further comprising a seal member provided between the one coupling and one of the first and second main body portions provided with the one coupling, enclosing the one of the first and second shaft portions, slidable in surface contact with at least one of the one coupling and the one of the first and second main body portions.

7. The endoscope according to claim 6, wherein the seal member is provided in an outer peripheral portion of the one coupling.

8. The endoscope according to claim 6, wherein the hardness of one coupling is higher than the hardness of the other coupling.

9. The endoscope according to claim 8, wherein the one coupling and the other coupling are different from each other in material.

10. The endoscope according to claim 8, wherein the one coupling and the other coupling are different from each other in surface treatment.

11. The endoscope according to claim 8, wherein the drive unit includes the one coupling, and the insertion portion includes the other coupling.

12. The endoscope according to claim 1, wherein the one of the convex and concave engaging portions provided on the other shaft portion is configured to be at the basic location while the bending portion does not bend.

13. The endoscope according to claim 2, wherein a gap portion is formed between the pair of insert guide surfaces and the pair of remove guide surfaces in the pair of guide members, and the width of the gap portion is larger than that of the guide portion.

14. The endoscope according to claim 2, wherein
the guide portion includes a guide pin protruding from the base end of the convex engaging portion, and
the guide pin is slidable with respect to the insert guide surface and the remove guide surface.

15. The endoscope according to claim 1, wherein
the narrow portion is configured to be abutted and slide to the pair of insert guide surfaces when the convex engaging portion is attached to the concave engaging portion from the base position, and
the wide portion is configured to be abutted and slide to the pair of remove guide surfaces when the convex engaging portion, engaged with the concave engaging portion, is detached from the concave engaging portion to the basic position.

* * * * *